United States Patent [19]
Steen et al.

[11] Patent Number: 5,984,904
[45] Date of Patent: Nov. 16, 1999

[54] SLEEVE FOR A SURGICAL INSTRUMENT

[75] Inventors: Mark E. Steen, Chino Hills; Robert J. Sullivan, Santa Margarita, both of Calif.

[73] Assignee: Bausch & Lomb Surgical, Inc., Claremont, Calif.

[21] Appl. No.: 08/697,353

[22] Filed: Aug. 22, 1996

[51] Int. Cl.⁶ ............................................. A61M 25/00
[52] U.S. Cl. ..................... 604/264; 604/22; 604/523; 606/169
[58] Field of Search ..................... 604/22, 240, 264, 604/272, 280, 523; 606/169

[56]  References Cited

U.S. PATENT DOCUMENTS

| | | |
|---|---|---|
| 2,432,641 | 12/1947 | Wilson . |
| 3,589,363 | 6/1971 | Banko et al. . |
| 3,659,607 | 5/1972 | Banko . |
| 3,693,613 | 9/1972 | Kelman . |
| 3,805,787 | 4/1974 | Banko . |
| 3,882,872 | 5/1975 | Douvas et al. . |
| 3,902,495 | 9/1975 | Weiss et al. . |
| 3,945,375 | 3/1976 | Banko . |
| 3,948,273 | 4/1976 | Sanders . |
| 4,099,147 | 7/1978 | McAvoy . |
| 4,180,074 | 12/1979 | Murry et al. . |
| 4,223,676 | 9/1980 | Wuchinich et al. . |
| 4,316,161 | 2/1982 | Moore et al. . |
| 4,370,131 | 1/1983 | Banko . |
| 4,428,748 | 1/1984 | Peyman et al. . |
| 4,504,264 | 3/1985 | Kelman . |
| 4,515,583 | 5/1985 | Sorich . |
| 4,516,398 | 5/1985 | Wuchinich . |
| 4,573,979 | 3/1986 | Blake . |
| 4,578,059 | 3/1986 | Fabricant et al. . |
| 4,609,368 | 9/1986 | Dotson, Jr. . |
| 4,634,420 | 1/1987 | Spinosa et al. . |
| 4,643,717 | 2/1987 | Cook et al. . |
| 4,652,255 | 3/1987 | Martinez . |
| 4,655,743 | 4/1987 | Hyde . |
| 4,674,502 | 6/1987 | Imonti . |
| 4,681,561 | 7/1987 | Hood et al. . |
| 4,705,500 | 11/1987 | Reimels et al. . |
| 4,764,165 | 8/1988 | Reimels et al. . |

(List continued on next page.)

FOREIGN PATENT DOCUMENTS

| | | |
|---|---|---|
| 269870 | 10/1987 | European Pat. Off. . |
| 375302 | 12/1989 | European Pat. Off. . |
| 376562 | 12/1989 | European Pat. Off. . |
| 94/23655 | 10/1994 | WIPO ...................................... 606/169 |

OTHER PUBLICATIONS

"Scleral and Corneal Burns During Phacoemulsification with Viscoelastic Materials," *ECRI*, 17(12):377–79 (Dec. 1988).

Polack et al., "The Phacoemulsification Procedure, III, Corneal Complications," *Invest. Ophthal. Vicual Sci.* 39–46 (1977).

Strobel et al., "Phaco–Emulsification and Planned ECCE: Intraoperative Differences in Intraocular Heating," *Eur. J. Implant, Ref. Surg.* 3:135–38 (1991).

Trade Journal Advertisement for new phaco tip from Storz Ophthalmics, *Ophthalmology Times*, Jun. 1, 1996, p. 34.

Advertisement for The Cobra Seal, ASCRS '96, Jun. 1, 1996, p. 85.

*Primary Examiner*—Corrine McDermott
*Assistant Examiner*—Cris L. Rodriguez
*Attorney, Agent, or Firm*—Banner & Witcoff Ltd.; Steven P. Scad; Rita D. Vacca

[57] ABSTRACT

A surgical sleeve which includes an array of spaced apart protuberances on an interior wall surface. The spaced protuberance reduce the surface contact between the sleeve and the tip and define a network of generally uniform channels through which fluid may flow, irrespective of pressure applied to the sleeve. As a result, the sleeve is able to provide fluid flow which is better able to remove heat from the tip and provide a more uniform irrigation of the eye.

27 Claims, 3 Drawing Sheets

U.S. PATENT DOCUMENTS

| | | |
|---|---|---|
| 4,787,889 | 11/1988 | Steppe et al. . |
| 4,808,154 | 2/1989 | Freeman . |
| 4,816,017 | 3/1989 | Hood et al. . |
| 4,816,018 | 3/1989 | Parisi . |
| 4,869,715 | 9/1989 | Sherburne . |
| 4,897,079 | 1/1990 | Zaleski et al. . |
| 4,922,902 | 5/1990 | Wuchinich et al. . |
| 4,983,160 | 1/1991 | Steppe et al. . |
| 5,015,227 | 5/1991 | Broadwin et al. . |
| 5,038,756 | 8/1991 | Kepley . |
| 5,059,204 | 10/1991 | Lawson et al. . |
| 5,084,009 | 1/1992 | Mackool . |
| 5,123,903 | 6/1992 | Quaid et al. . |
| 5,151,083 | 9/1992 | Pichler . |
| 5,151,084 | 9/1992 | Khek . |
| 5,162,044 | 11/1992 | Gahn et al. . |
| 5,188,589 | 2/1993 | Wypych . |
| 5,199,943 | 4/1993 | Wypych . |
| 5,242,385 | 9/1993 | Strukel . |
| 5,282,786 | 2/1994 | Ureche . |
| 5,286,256 | 2/1994 | Mackool . |
| 5,354,265 | 10/1994 | Mackool . |
| 5,417,654 | 5/1995 | Kelman . |
| 5,464,389 | 11/1995 | Stahl . |
| 5,478,338 | 12/1995 | Reynard . |
| 5,486,162 | 1/1996 | Brumbach . |
| 5,496,342 | 3/1996 | Urich . |
| 5,505,693 | 4/1996 | Mackool . |
| 5,681,296 | 10/1997 | Ishida ................................ 604/282 |

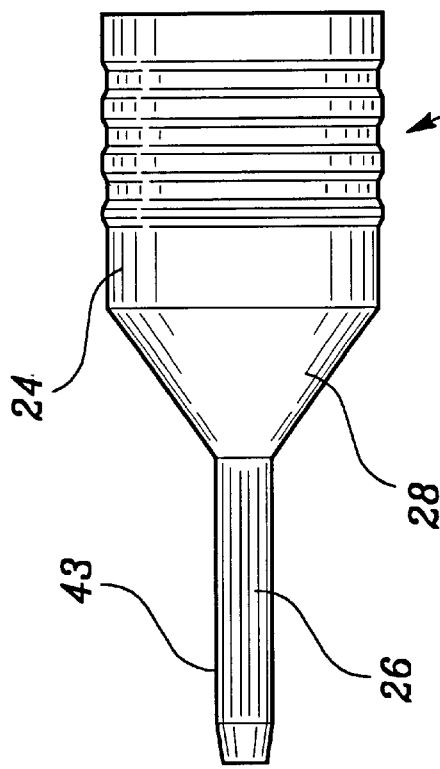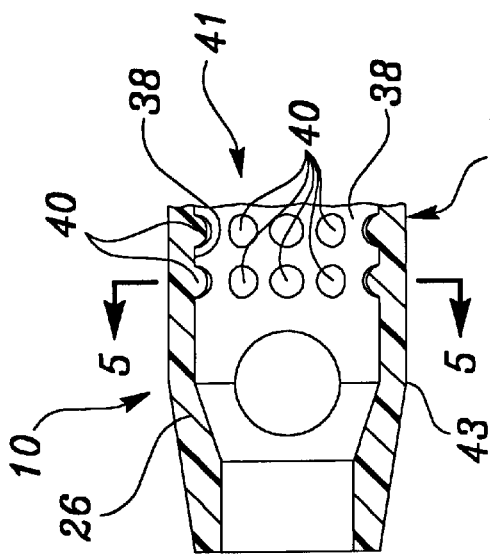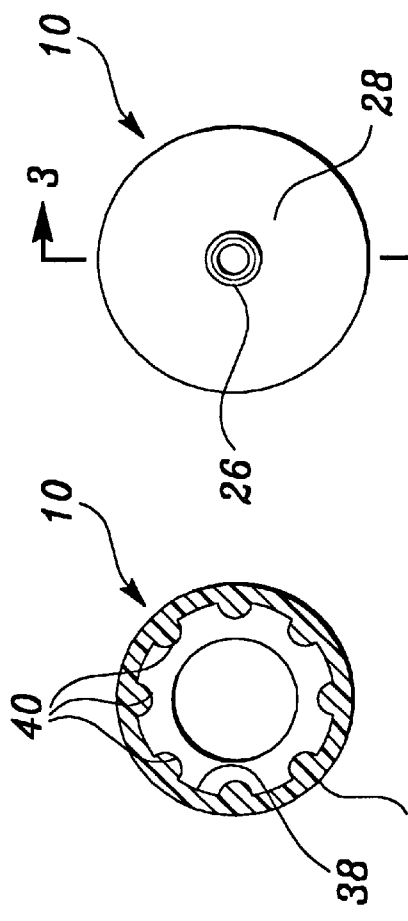

SLEEVE FOR A SURGICAL INSTRUMENT

FIELD OF THE INVENTION

The present invention pertains to a sleeve for attachment to a surgical instrument for removing the natural lens of an eye. The surgical sleeve surrounds a slender cutting tip of the instrument and defines a fluid conduit about the tip.

BACKGROUND OF THE INVENTION

The natural crystalline lens of the eye plays a primary role in focusing light onto the retina for proper vision. However, the natural lens at times is replaced with an artificial lens to make a refractive correction or because of damage or injury to the natural lens. Under these circumstances, the natural lens is surgically removed from the eye.

Surgical procedures which require only a small incision to be made in the eye have been developed for removing the natural lens. In accordance with these procedures, a slender cutting tip of a surgical instrument is inserted through the incision to engage the natural lens. The cutting tip is typically subjected to ultrasonic vibrations to emulsify the lens (e.g., phacoemulsification). The emulsified portions of the lens are then aspirated from the eye through a central bore in the tip. A silicone sleeve surrounds the tip to define an annular conduit for the passage of fluid to cool the tip and irrigate the eye.

During an operation, the surgical instrument is manipulated to remove the entire lens. Because of this movement, the sleeve can at time become pinched between the tip and the tissue of the eye. The frictional contact between the sleeve and the vibrating tip can generate a significant mount of heat in the sleeve. The tissue of the eye is sensitive and can be damaged by the heat in a matter of a few seconds.

Efforts to alleviate the risk of burning the tissue have included such devices as described in U.S. Pat. No. 4,808,154 to Freeman. The Freeman device has longitudinal ribs formed along the interior of the sleeve. The ribs are intended to isolate portions of the wall from the tip to reduce the frictional contact, and provide channels to direct fluid flow about the tip. However, if the conduit becomes partially occluded by material within the eye, the flow of fluid along an entire length of the tip can be lost. Moreover, manipulation of the surgical instrument nay cause the sleeve to twist, which results in the ribs being drawn together thereby closing the channels. Clearly, the partial or complete blocking of the fluid passages will only exacerbate the problems associated with overheating of the surgical site.

U.S. Pat. No. 5,188,589 to Wypych discloses a sleeve wherein the interior surface surrounding the tip is provided with a rough texture of random bangs and pits. The bumps and pits are formed by acid etching or bead or sand blasting of the mold to form a roughened texture having a relieved or sandpaper-like appearance. This construction reduces the frictional contact between the sleeve and the tip, and provides passages (i.e., the pits) through which the fluid can flow about the tip even when compressed. However, the construction of the roughened texture creates blind and constricted passages which increase fluid resistance and hamper proper fluid flow.

SUMMARY OF THE INVENTION

The present invention pertains to a sleeve for use with a surgical instrument having a slender cutting tip for removing the natural lens from an eye. The surgical sleeve includes a contoured interior surface which provides superior performance in reducing the frictional contact between the sleeve and tip, and maximizes the effect of the fluid flow about the tip.

In accordance with the present invention, the sleeve is provided with an array of protuberances on an interior wall surface. The spaced protuberances reduce the surface contact between the sleeve and the tip, and define a network of generally uniform channels through which the fluid may flow, irrespective of the pressure lied to the sleeve. As a result, the entire tip is coated in a constant stream of coolant fluid about its entire surface in a steady, uniform manner. The uniform network of channels about each protuberance reduces fluid resistance and provides a more uniform irrigation of the eye.

BRIEF DESCRIPTION OF THE DRAWINGS

FIG. 1 is a side view of a sleeve in accordance with the present invention.

FIG. 2 is a front end view of the sleeve.

FIG. 3 is a cross-sectional view taken along line 3—3 in FIG. 2.

FIG. 4 is a partial, enlarged sectional view of the portion identified by line 4 in FIG. 3.

FIG. 5 is a cross-sectional view taken along line 5—5 in FIG. 4.

DETAILED DESCRIPTION OF THE PREFERRED EMBODIMENTS

Figure 6:
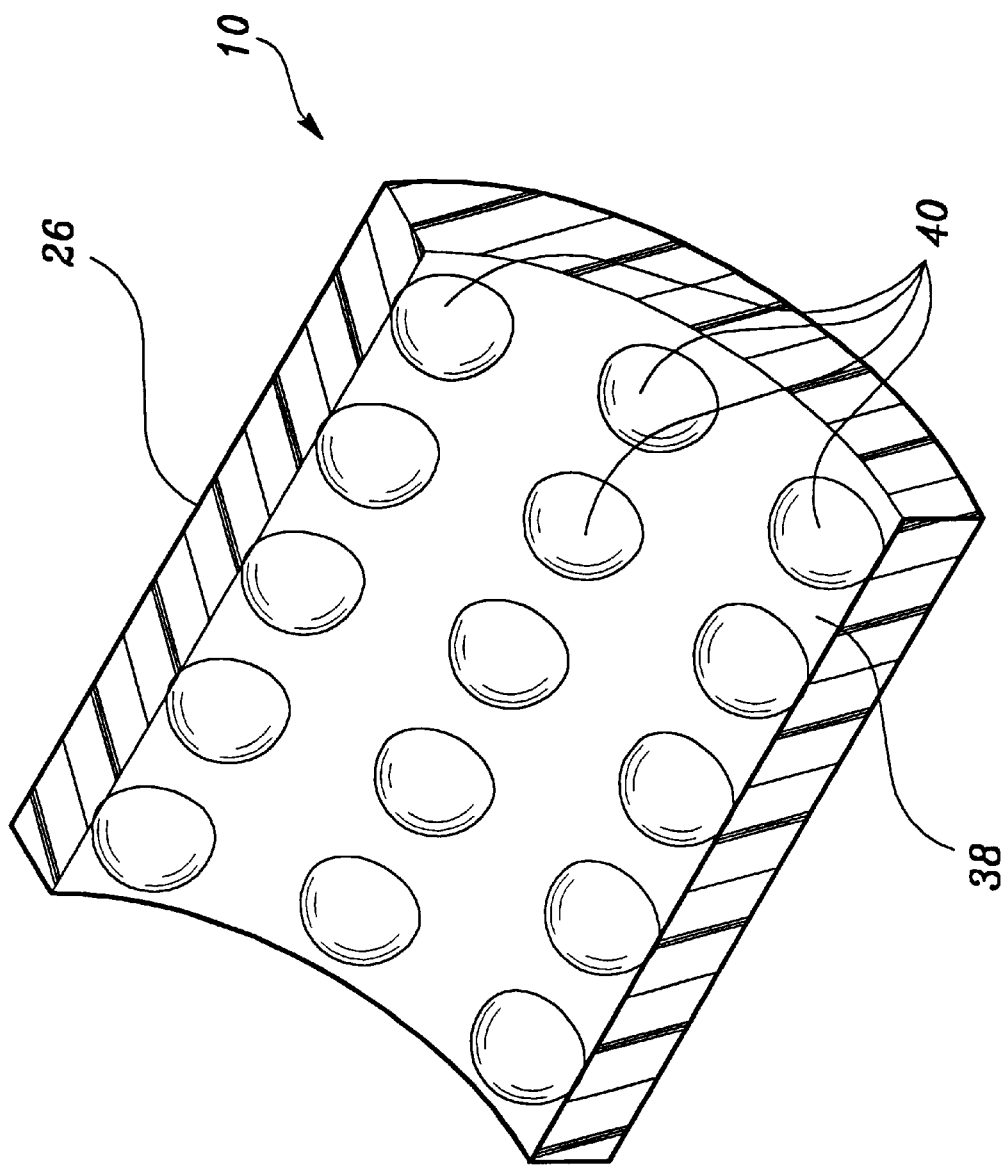
FIG. 6 is an enlarged partial perspective view of the interior of the cannula of the sleeve.
Figure 7:
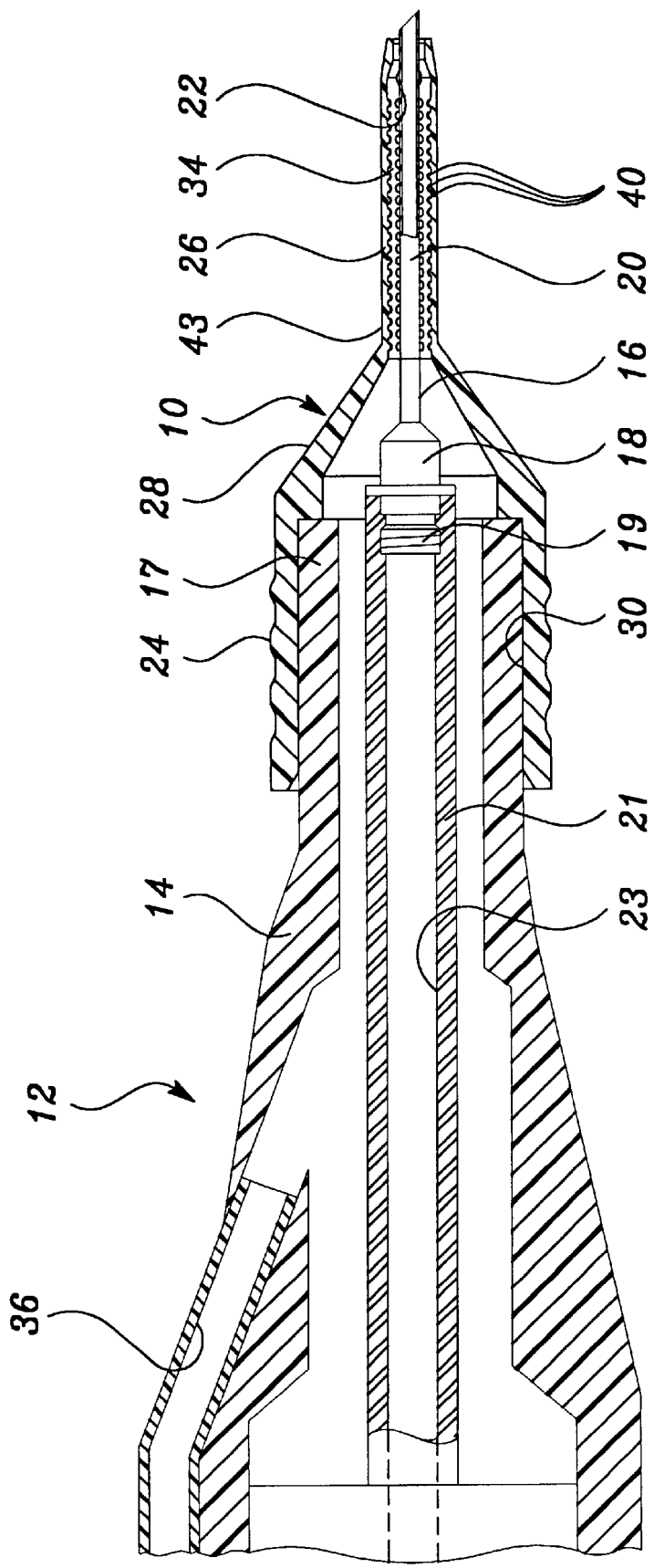
FIG. 7 is a sectional view of the sleeve mounted on a surgical instrument.

The present invention pertains to a sleeve 10 designed for attachment to a surgical instrument having a slender cutting tip for removing the natural lens of an eye. One such common surgical instrument is a phacoemulsification device 12 (FIG. 7). In general, device 12 includes a casing 14 to be grasped and manipulated by a surgeon, and a slender cutting tip 16 which projects from a distal end 17 of the casing.

Tip 16 has a slender cutting shank 20 and a base 18 with a threaded stud 19 for connection to a core assembly 21 contained within the casing. When activated, core 21 ultrasonically vibrates tip 16 in an axial direction to emulsify the natural lens. Tip 16 has a central bore 22 coupled to a passage 23 in core 21. Passage 23 is, in turn, attached to a vacuum source (not shown) to aspirate the emulsified lens fragments from the eye.

Sleeve 10 includes a base 24, a cannula 26, and a transition segment 28 with a funnel-like configuration connecting the cannula and the base (FIGS. 1–5 and 7). The sleeve is preferably a unitary molded composed of silicone. Nevertheless, the sleeve could be formed as an integrated assembly of multiple pieces, or formed with other pliable materials which are resilient or semi-rigid and suitable for insertion into an eye during surgery.

Base 24 is a hollow segment that forms the proximal end of the sleeve. The interior surface 30 of base 24 is cylindrical to slide over the distal end 17 of casing 14. Alternatively, the base could be internally threaded for threaded attachment to the casing. Cannula 26 is a narrow, pliable tube which encircles the cutting shank 20 of tip 16 and defines an annular conduit 34 about tip 16. Fluid is passed into passage 36 in casing 14 from a source (not shown), and directed to flow through annular conduit 34 and into the eye. The fluid is provided to cool the instrument and to irrigate the eye during the operation.

Cannula 26 preferably has a circular cross-sectional configuration, although other shapes may also be used. In either case, the cannula has a generally smooth interior wall 38 provided with an array of spaced apart protuberances 40 (FIGS. 4–7). Protuberances 40 preferably project from a generally smooth background surface which is uniformly recessed about each protuberance. The protuberances have rounded shapes, which in the preferred construction are generally conical. In this way, contact with the tip is minimized when cannula 26 is pressed against the tissue of the eye. In one preferred construction, the protuberances are about 0.003 inches in height, and out 0.010 inches in diameter along interior wall 38. Protuberances 40 are preferably aligned in columns 41 extending parallel to the longitudinal axis of tip 26, and transverse rows 42 extending perpendicular to the columns. The columns preferably extend along substantially the entire length of the cannula; although the protuberances are only needed along the portions of the cannula expected to be positioned between the eye tissue and the tip (i.e., in the region where the sleeve is likely to be pinched between the tip and the tissue of the eye). In one preferred construction, the protuberances are about 0.0.15 inches center-to-center along the columns, and spaced apart radially about 36° center-to-center along the rows. Accordingly, the spacing between adjacent protuberances 40 in the preferred embodiment is equal to about one-half the width of each protuberance in order to define a network of open channels through which the fluid may flow without undue resistance. Nevertheless, other arrangements, spacings and sizes of protuberances could be used to achieve the same objective.

In use, sleeve 10 and tip 16 are inserted through a small incision in the eye. Ordinarily cannula 26 is snugly received into the incision such that tissue of the eye engages the exterior surface 43 of the cannula. As the surgeon manipulates the instrument, tip 16 at times presses cannula 26 against the adjacent tissue of the eye. In the present invention, protuberances 40 form an array of point contacts which engage the side of the tip and minimize the surface area contact between the sleeve and the cannula. As a result, the generation of heat due to the frictional contact of the vibrating tip against the sleeve is minimized.

Further, the spaced apart protuberances 40 on interior wall 38 form a network of substantially uniform, consistent channels 44 through which the fluid flow. The channels extend about each protuberance 40 in longitudinal and transverse directions for uniform flow of the fluid at each protuberance such that the formation of blind, constricted, or circuitous fluid passageways is avoided. As a result, sleeve 10 creates less fluid resistance and provides for a more uniform flow of the fluid about the tip and into the eye as compared to the prior art, irrespective of the compression of the cannula. In this way, the fluid flow is better able to remove the heat from the tip and to provide a more uniform irrigation of the eye than previously attained.

The above-discussion concerns the preferred embodiments of a sleeve adapted for attachment to a surgical instrument provided with a cutting tip that is driven to remove the natural lens of an eye. Variations in the drive and construction of the surgical instrument and in the sleeve construction may be made without departing from the spirit and broader aspects of the invention as defined in the claims.

We claim:

1. A surgical sleeve for use with an instrument to perform eye surgery, wherein the instrument includes a casing and a slender cutting tip projecting from the casing, said surgical sleeve comprising a one-piece tubular, pliable body including a base having a free end, said free end having a cavity adapted to receive the casing, and a cannula extending outward from said base, said cannula having a passage narrower than said cavity to receive and define a conduit about the cutting tip, said cannula including an array of protuberances projecting from an interior wall surface and spaced apart in longitudinal and transverse directions so as to define a network of generally uniform channels extending between adjacent protuberances for fluid flow about each protuberance in longitudinal and transverse directions.

2. A surgical sleeve in accordance with claim 1 in which said protuberances are rounded for minimal contact with the tip when the cannula is compressed against tissue of the eye.

3. A surgical sleeve in accordance with claim 2 in which said protuberances have generally conical shapes.

4. A surgical sleeve in accordance with claim 1 in which said protuberances are arrayed in a uniform pattern.

5. A surgical sleeve in accordance with claim 1 in which said protuberances are aligned in columns extending parallel to the longitudinal axis of said cannula.

6. A surgical sleeve in accordance with claim 5 in which said protuberances are further aligned in rows extending perpendicular to the longitudinal axis of said cannula.

7. A surgical sleeve in accordance with claim 1 in which said protuberances are aligned in rows extending perpendicular to the longitudinal axis of said cannula.

8. A surgical sleeve in accordance with claim 1 in which said interior wall surface of said cannula is generally smooth and uniformly recessed about each protuberance.

9. A surgical sleeve in accordance with claim 1 in which each protuberance has a width and is spaced from adjacent protuberances in longitudinal and transverse directions by a space equal to at least about one-half the width of each protuberance to define a network of open fluid channels about each protuberance.

10. A surgical sleeve in accordance with claim 9 in which each said protuberance has a width equal to about 0.01 inches.

11. A surgical sleeve in accordance with claim 9 in which said protuberances are aligned in columns extending parallel to the longitudinal axis of said cannula.

12. A surgical sleeve in accordance with claim 11 in which said protuberances are further aligned in rows extending perpendicular to the longitudinal axis of said cannula.

13. A surgical sleeve in accordance with claim 9 in which said protuberances are aligned in rows extending perpendicular to the longitudinal axis of said cannula.

14. A surgical sleeve in accordance with claim 9 in which said interior wall surface of said cannula is generally smooth and uniformly recessed about each protuberance.

15. A surgical instrument for eye surgery comprising:

a casing;

a cutting tip projecting from the casing; and a surgical sleeve comprising a tubular, pliable body having a base and a cannula, said base being attached to the casing such that said cannula extends outward from said base and encircles the cutting tip to define a conduit, said cannula including an array of protuberances projecting from an interior wall surface and spaced apart in longitudinal and transverse directions so as to define a network of generally uniform channels extending between adjacent protuberances for fluid flow about each protuberance in longitudinal and transverse directions.

16. An instrument in accordance with claim 15 in which said protuberances of said surgical sleeve are rounded for minimal contact with the tip when the cannula is compressed against tissue of the eye.

17. A surgical instrument in accordance with claim 15 in which said protuberances of said surgical sleeve are arrayed in a uniform pattern.

18. A surgical instrument in accordance with claim 17 in which said protuberances of said surgical sleeve are aligned in columns extending parallel to the longitudinal axis of said cannula.

19. A surgical instrument in accordance with claim 18 in which said protuberances of said surgical sleeve are further aligned in rows extending perpendicular to the longitudinal axis of said cannula.

20. A surgical instrument in accordance with claim in 17 which said protuberances of said surgical sleeve are aligned in rows extending perpendicular to the longitudinal axis of said cannula.

21. A surgical instrument in accordance with claim 15 further including an inlet port for supplying fluid into said sleeve, through said conduit, and into an eye, a central passage in said cutting tip, and an outlet port for supplying a vacuum to aspirate material from the eye and through said central passage.

22. A surgical instrument for eye surgery comprising:
   a casing;
   a slender cutting tip projecting from the casing; and
   a surgical sleeve comprising a tubular, pliable body having a base and a narrow cannula, said base being attached to the casing so that said cannula encircles the cutting tip to form a conduit, said cannula having an interior surface including an array of spaced apart protuberances, each protuberance having a width and being spaced from adjacent protuberances in longitudinal and transverse directions by a space equal to at least about one-half the width of each protuberance to define a network of open fluid channels about each protuberance.

23. A surgical instrument in accordance with claim 22 in which each said protuberance of said surgical sleeve has a width equal to about 0.01 inches.

24. A surgical sleeve in accordance with claim 1 which in said base includes a generally cylindrical portion at said free end and a tapering transition portion between said generally cylindrical portion and said cannula.

25. A surgical sleeve in accordance with claim 1 which in said base has a length which is about the same as said cannula.

26. A surgical sleeve for use with an instrument to perform eye surgery, wherein the instrument includes a casing and a slender cutting tip projecting from the casing, said surgical sleeve comprising a tubular, pliable body including a cannula having a generally cylindrical configuration so as to encircle the cutting tip and define a conduit, and a base widening from said cannula and having a cavity adapted to receive and attach to the casing, said base and said cannula having about the same length, said cannula including an array of protuberances projecting from an interior wall surface and spaced apart in longitudinal and transverse directions so as to define a network of generally uniform channels extending between adjacent protuberances for fluid flow about each protuberance in longitudinal and transverse directions.

27. A surgical sleeve in accordance with claim 26 in which said base includes a generally cylindrical portion at said free end and a tapering transition portion between said generally cylindrical portion and said cannula.

* * * * *